United States Patent
Holt

(12)
(10) Patent No.: US 6,428,566 B1
(45) Date of Patent: Aug. 6, 2002

(54) FLEXIBLE HOOP AND LINK SHEATH FOR A STENT DELIVERY SYSTEM

(75) Inventor: Vivianne M. Holt, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 67 days.

(21) Appl. No.: 09/703,859

(22) Filed: Oct. 31, 2000

(51) Int. Cl.[7] .............................. A61F 2/06; A61B 1/00; A61M 25/16; A61M 25/18; A61M 25/00
(52) U.S. Cl. ................. 623/1.11; 623/1.23; 600/139; 600/141; 604/523; 604/525; 604/534; 604/535
(58) Field of Search .................... 604/523, 524, 604/526, 525, 534, 535; 600/585, 139, 141, 146–151; 623/1.11, 1.23; 606/108

(56) References Cited

U.S. PATENT DOCUMENTS

| | | | | |
|---|---|---|---|---|
| 4,790,294 A | * | 12/1988 | Allred, III et al. | 128/4 |
| 5,643,278 A | * | 7/1997 | Wijay | 606/198 |
| 5,653,748 A | * | 8/1997 | Strecker | 623/1 |
| 5,961,536 A | * | 10/1999 | Mickley et al. | 606/194 |
| 6,306,163 B1 | * | 10/2001 | Fitz | 623/1.11 |
| 6,334,866 B1 | * | 1/2002 | Wall | 623/1.12 |
| 6,334,867 B1 | * | 1/2002 | Anson | 623/1.13 |

* cited by examiner

Primary Examiner—Dinh X. Nguyen
Assistant Examiner—Cheryl Miller
(74) Attorney, Agent, or Firm—Fulwider Patton Lee & Utecht, LLP

(57) ABSTRACT

A delivery sheath including a series of longitudinally spaced apart retainer rings interconnected by flexible links. This configuration provides for sections of reduced cross-sectional area along the length of the sheath, thus increasing flexibility in those sections and in the overall sheath. The reduction of the cross-sectional area of the sheath also effectively reduces the area of contact between the inside surface of the sheath and the outside surface of the compressed stent. This reduction in contact area serves to reduce the frictional force generated as the sheath is retracted relative to the stent during deployment.

25 Claims, 5 Drawing Sheets

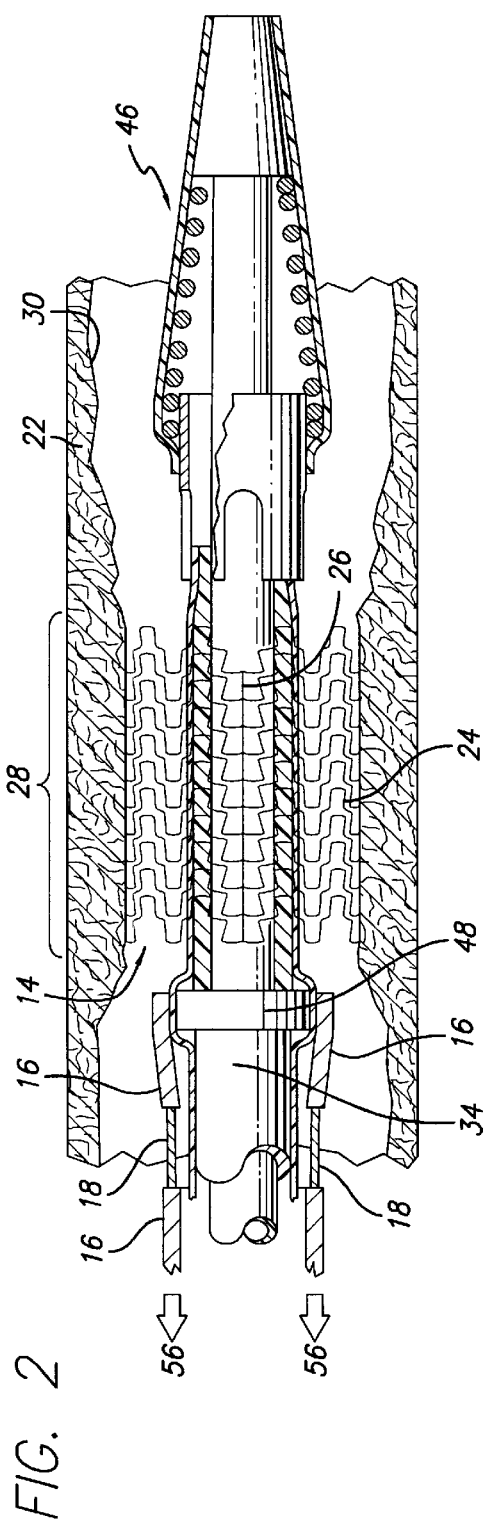
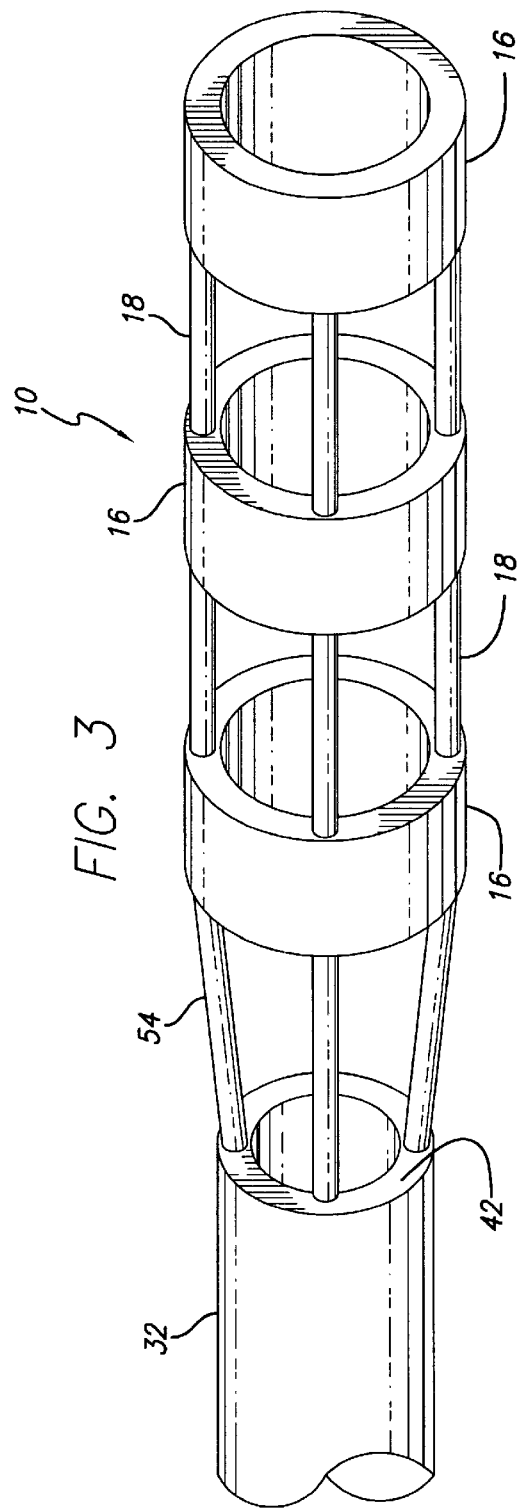

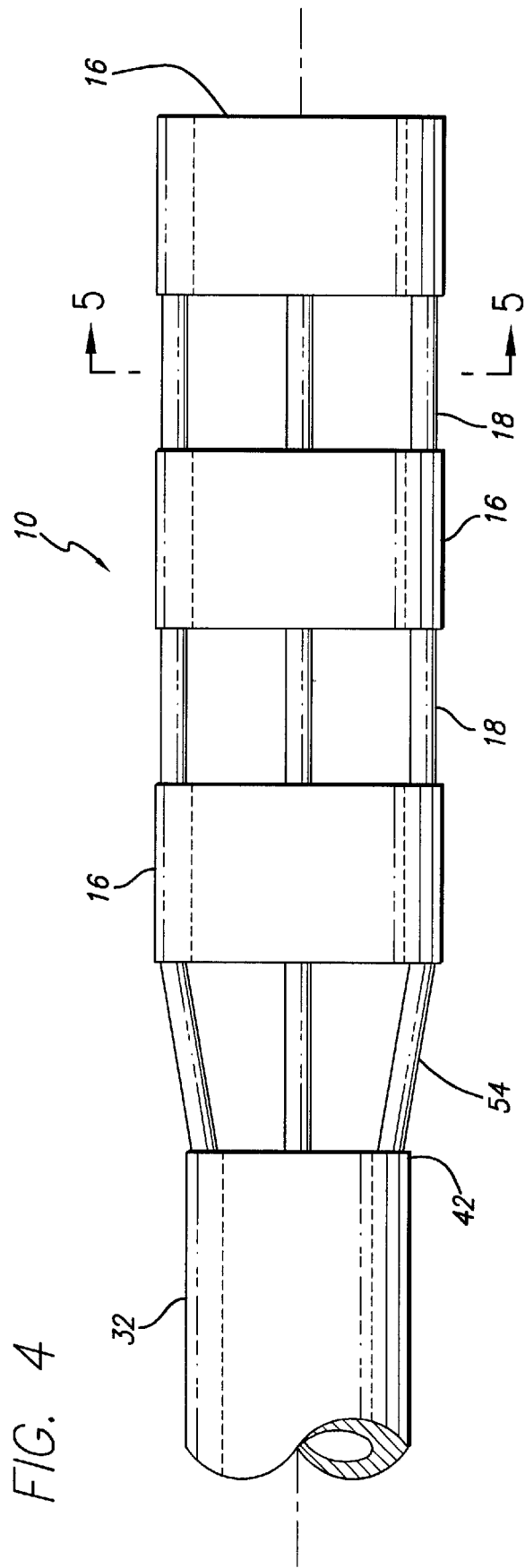
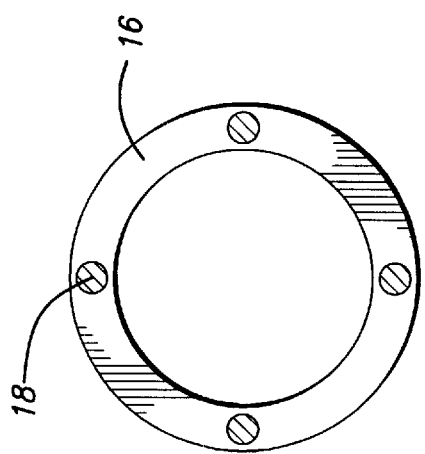
FIG. 4
FIG. 5

FLEXIBLE HOOP AND LINK SHEATH FOR A STENT DELIVERY SYSTEM

BACKGROUND OF THE INVENTION

The present invention relates to expandable endoprosthesis devices, generally called stents, which are adapted to be implanted into a patient's body lumen, such as a blood vessel, to maintain the patency thereof. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis.

Stents are generally tubular shaped devices which function to hold open and sometimes expand a segment of a blood vessel or other arterial lumen, such as a coronary artery. Stents are usually delivered in a radially compressed condition to the target site and then deployed at that location into a radially expanded condition to support the wall of the vessel and help maintain it dilated. They are particularly suitable for urging a segment of a dissected arterial lining radially outwardly in a lumen to maintain a fluid passageway there through.

A variety of devices are known in the art for use as stents and have included coiled wires in a variety of patterns that are expanded after being placed intraluminally on a balloon catheter; helically wound coiled springs manufactured from an expandable heat sensitive metal; and self-expanding stents inserted in a compressed state for deployment into a body lumen.

Prior art stents typically fall into two general categories of construction. The first type of stent is expandable upon application of a controlled force, often through the inflation of the balloon portion of a dilatation catheter which, upon inflation of the balloon or other expansion means, expands the wall of the compressed stent to a larger diameter to be left in place within the artery at the target site. The second type of stent is a self-expanding stent formed, for example, from shape memory metals such as nickel-titanium (NiTi) alloys, which will respond to elevated temperature or the like to expand from a radially compressed state when the stent is advanced out of the distal end of the delivery catheter into the blood vessel. Such stents manufactured from expandable heat sensitive materials allow for phase transformations of the material to occur, resulting in the expansion and contraction of the stent. Other self-expanding stents may use stress-induced martensite (SIM) alloys to allow the stent to move between contracted and expanded positions.

Typical stent delivery systems for implanting expandable stents at the target site generally include a dilatation catheter having an inflatable balloon or other expandable means mounted at the distal end thereof. The expandable stent is radially compressed onto the balloon for delivery within a body lumen. Some prior art stent delivery systems for implanting balloon expandable stents utilize an outer delivery sheath that is initially placed over the compressed stent prior to delivery. A delivery sheath is sometimes used to prevent the compressed stent from moving axially along the balloon portion of the dilatation catheter while being advanced within the patient's vasculature. Once the catheter is in place, the physician can retract the outer sheath to expose the stent and expandable balloon. The physician can then inflate the balloon portion of the dilatation catheter to cause the compressed stent to expand radially to a larger diameter to be left in place within the artery at the target site.

In the case of implanting self-expanding stents at the target site, typical delivery systems include an inner lumen upon which the compressed or collapsed stent is mounted and an outer restraining sheath that is initially placed over the compressed stent prior to deployment. When the stent is to be deployed in the body vessel, the outer sheath is moved in relation to the inner lumen to "uncover" the compressed stent, allowing the stent to move to its expanded condition. Some delivery systems utilize a "push-pull" technique in which the outer sheath is retracted while the inner tubing is pushed forward. Still other systems use an actuating wire that is attached to the outer sheath. When the actuating wire is pulled to retract the outer sheath and deploy the stent, the inner tubing must remain stationary, thereby preventing the stent from moving axially within the body lumen.

Prior art stent delivery systems are benefitted by the function of the delivery sheath in preventing the collapsed stent from moving axially along the inner lumen of the delivery catheter while being advanced within the patient's vasculature. In addition, sometimes the stent cannot be deployed for a variety of reasons, so it must be able to be pulled back into the guiding catheter without being "stripped off" of the dilatation or delivery catheter. Further, despite the care given during placement, stents can become dislodged from the delivery system. The consequences of losing a stent range from embarrassment to a life threatening situation requiring immediate surgery. The use of a delivery sheath can help alleviate such problems.

The delivery sheath also helps prevent the stent from abrading the body lumen wall as the stent is being manipulated into the target area. With no delivery sheath, the struts of the stent would be exposed to the walls of the patient's vasculature and could possibly cause trauma to the walls or cause pieces of plaque to break from the stenosis. Abrasive forces in the area of the stenosis are not desirable due to the possible formation of embolic debris that would be released into the patient's blood stream. Such debris could possibly occlude smaller blood vessels leading to vital organs such as the brain. Thus, for a variety of reasons, the outer sheath remains in place over the compressed stent until the physician has manipulated the catheter into the proper location within the patient's vasculature. Once in position, the physician can retract the outer sheath to expose the stent and allow it to safely expand within the body lumen at the target site.

It follows that it is beneficial for the delivery sheath to have a low profile with no obtrusions and that the sheath be made of a low-friction, flexible material. Such construction would facilitate the insertion of the stent delivery system into small inner diameter guide catheters and body lumens and would minimize trauma to the lumens as the delivery system is being maneuvered into tight, difficult-to-reach areas in the patient's vasculature.

When used with a self-expanding stent delivery system, the delivery sheath must serve an additional purpose of resisting the radial force being applied to the sheath by the stent as it is held in its collapsed condition. In some self-expanding stent designs, the radial force applied by a collapsed stent can be quite substantial. As a result, the delivery sheath must have sufficient strength to support the collapsed stent against expansion. Additionally, since a stent delivery system may be placed in storage for a considerable length of time, the sheath must be capable of restraining the stent during that period. The prolonged exposure of the sheath to an expansive force can ultimately deform the sheath (referred to as creep), which can render the delivery system useless for implantation in a patient.

The path to the deployment site within a patient's body lumen may be relatively tortuous, involving navigation through various curves and turns of the patient's vasculature, which requires longitudinal flexibility in order to accommodate the turns without inflicting trauma to the walls of the lumen. In the past, this requirement for flexibility dictated a relatively thin wall sheath and placed the constraint on the designer trading off sheath strength for flexibility. There thus exists a need for a sheath which affords sufficient radial strength to maintain the self-expanding stent compressed during deployment, but yet has sufficient flexibility along the longitudinal axis to accommodate navigation through various curves and turns in the body lumen.

Moreover, in some prior art self-expanding stent delivery systems, the frictional force of the sheath against the stent can cause the stent to somewhat contract axially against the resiliency of the undulations of the stent structure, thus causing the stent to store energy. Such stored energy can be released as the sheath is fully retracted off the length of the stent, causing the stent to move or "jump" distally from the end of the sheath, thereby shifting it from the desired position and resulting in inaccurate placement in the body vessel. The amount of energy stored is a function of the flexibility of both the stent and the sheath and frictional forces generated between them. Therefore, it is important that the delivery sheath allow the self-expanding stent to slide relatively freely relative to the sheath as the sheath is being retracted in order to achieve smooth and accurate deployment of the stent.

What has been needed and heretofore unavailable is a delivery sheath to be utilized in conjunction with a stent delivery system that has increased flexibility and reduced frictional contact with the stent, while still effectively retaining the stent and preventing the stent from contacting and injuring the body lumen wall during manipulation of the delivery system into the treatment area. The present invention disclosed herein satisfies these and other needs.

SUMMARY OF THE INVENTION

The present invention is directed to a delivery sheath for use in conjunction with a stent delivery system which has increased flexibility and reduced frictional contact with the stent. The delivery sheath is uniquely composed of a series of longitudinally spaced apart retainer rings interconnected by flexible links. This configuration provides for sections of reduced cross-sectional area along the length of the sheath, thus increasing flexibility in those sections and overall in the sheath.

The reduction of the cross-sectional area of the delivery sheath of the present invention achieved by incorporating the flexible links into the sheath structure can also serve to effectively reduce the area of contact between the inside surface of the sheath and the outside surface of the compressed stent. This reduction in contact area serves to reduce the frictional force generated between the sheath and the stent as the sheath is retracted relative to the stent during deployment. Such reduction in friction is particularly advantageous for delivery of self-expanding stents, where frictional energy can be stored axially in the stent as the sheath is retracted, causing the stent to move or "jump" forward during deployment, thus possibly resulting in inaccurate stent placement.

One conventional stent delivery system with which the sheath of the present invention cooperates includes an elongated, flexible catheter body comprised of an inner tubular member that extends within an outer tubular member in a coaxial arrangement. In the case of balloon expandable stents, the inner tubular member includes an inflatable balloon or other expansion means at its distal end. The outer tubular member has the delivery sheath mounted at its distal end to cover the stent as the delivery system is advanced within the patient's vasculature and also, for self-expanding stents, to retain the stent in a radially compressed delivery position on the inner tubular member until deployment. The outer tubular member and delivery sheath are slidably retractable relative to the inner tubular member in order to deploy the stent to its expanded condition within the body lumen.

Therefore, the present invention provides a delivery sheath with increased flexibility and reduced friction to cooperate with the stent delivery system to more easily negotiate tortuous anatomy within a patient's vasculature and more accurately deploy the stent at the target site. Ultimately, the benefits of the present invention is safer and more effective stent delivery. Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 2 is a longitudinal sectional view showing the delivery sheath of FIG. 1 retracted and the stent expanded within the body vessel;

FIG. 3 is an enlarged, partial perspective view of an outer tubular member included in the self-expanding stent delivery system shown in FIG. 1;

FIG. 4 is a side view of the outer tubular member shown in FIG. 3;

FIG. 5 is a sectional view taken along lines 5—5 of FIG. 4;

DETAILED DESCRIPTION OF THE PREFERRED EMBODIMENTS

Figure 1:
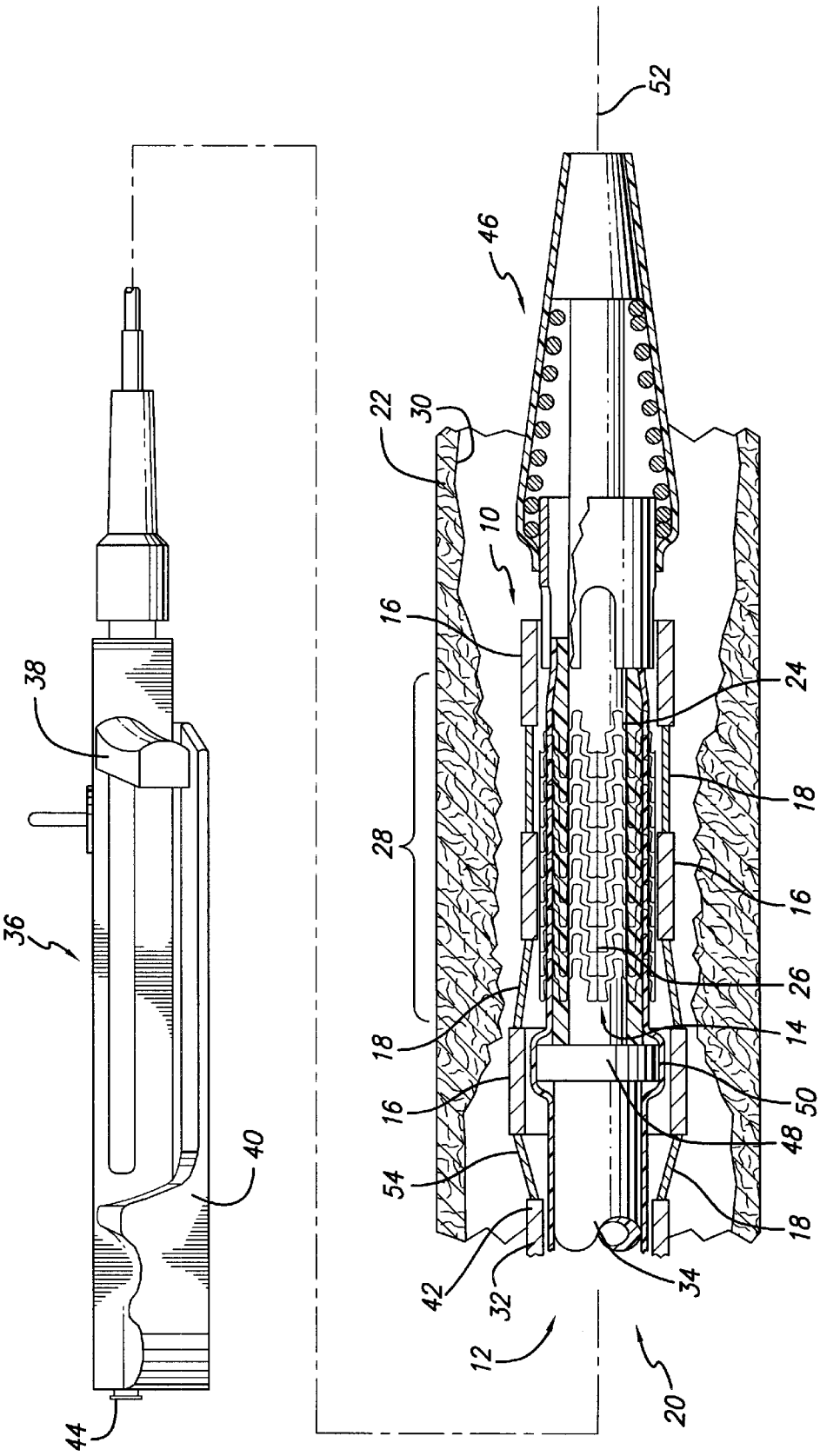
FIG. 1 is a broken side view, partially in section and enlarged in scale, depicting one particular self-expanding stent delivery system incorporating a delivery sheath of the present invention disposed within a body vessel.

The present invention is directed to a delivery sheath for use in conjunction with a stent delivery system having tubular retainer rings interconnected by flexible links to provide increased flexibility of the stent delivery system and reduced frictional contact between the sheath and the stent. While the present invention is described in detail as used with a particular self-expanding stent delivery system, those skilled in the art will appreciate that the sheath can be used in conjunction with balloon expandable stents as well as other types of stents and stent delivery systems. Furthermore, although the present invention is described as applied to the arteries of a patient, it will be appreciated that it can be used in other body lumens as well.

Referring now to the drawings in which reference numerals represent like or corresponding elements across the drawings, and particularly FIGS. 1–5, a delivery sheath 10 of the present invention is illustrated in a delivery system, generally designated 12, and may be employed to deliver a self-expanding stent 14. In accordance with the present invention, the delivery sheath 10 is highly flexible and has minimal frictional contact with the stent 14. The delivery sheath 10 is uniquely composed of a series of longitudinally spaced apart retainer rings 16 interconnected by flexible links 18. This configuration serves to create sections of reduced cross-sectional area along the length of the sheath 10, thereby increasing the flexibility in those sections and reducing the frictional contact between the sheath and the stent, thus providing a safer and more effective stent delivery system.

The stent delivery system 12 includes an elongated delivery catheter 20 for delivering and deploying the compressed stent 14 within an artery 22 or other body vessel. A typical self-expanding stent is shown generally comprised of a number of radially expandable cylindrical elements 24, or undulations disposed generally coaxially and connected by interconnecting longitudinal members 26 disposed between adjacent cylindrical elements. For illustrative purposes, the artery shown in FIGS. 1 and 2 has an area of treatment 28, in which atherosclerotic plaque of a stenosis is to be compressed against the inside wall 30 of such artery in order to increase the diameter of the occluded area 28. The stent, shown expanded within the artery in FIG. 2, is implanted to compress the stenosis to help hold open the diseased area of the artery, and to hopefully delay or prevent restenosis.

With continued reference to FIG. 1, the delivery catheter 20 of the stent delivery system 12 includes an outer tubular member 32, coaxially disposed about, and configured to move slidably along, an inner tubular member 34. A deployment control assembly 36 is integrally attached to the proximal end of the delivery catheter. The proximal end of the outer member of the delivery catheter is attached to a pull-back handle 38 that may be drawn proximally relative to a hand grasp housing 40 to retract the outer member. The delivery sheath 10 of the present invention is integral with the distal end 42 of the outer tubular member 32. The inner tubular member 34 includes a luer fitting 44 at its proximal end rigidly attached to the proximal end of the hand grasp housing (FIG. 1) for receiving a guide wire (not shown) which can be used to place the catheter 20 in the proper location.

Referring still to FIG. 1, a stent delivery tip 46 is formed at the distal end 42 of the elongated shaft of the inner tubular member 34 for the purpose of mounting the stent 14 for delivery. The shaft includes a radiopaque marker 48 having a shoulder that acts as a stop to the proximal end of the stent to prevent proximal travel of the stent on the inner tubular member. The space between the delivery tip 46 and radiopaque marker 50 forms a mounting region 52 for the stent. The radiopaque marker 48 can be used for the purpose of locating the relative position of the proximal end of the stent during delivery to the treatment area 28. In the embodiment shown herein, the radiopaque marker is encapsulated within heat shrink tubing 50 that is configured to secure the position of the radiopaque marker 48 relative to the distal end of the elongated shaft and to provide reduced frictional contact between the inner tubular member 34 and the inside surface of the delivery sheath 10.

Referring now to FIGS. 3–5, in one embodiment of the present invention, the delivery sheath 10 includes three longitudinally spaced apart retainer rings 16 interconnected respectively by four flexible links 18. As is better depicted in FIGS. 4 and 5, such links 18 are arrayed roughly ninety degrees apart and are longitudinally disposed between the respective retainer rings 16 generally parallel to the central axis 52 of the outer tubular member 32. Similarly, four attachment links 54 are disposed between the most proximal retainer ring and the distal end of the elongated tubular member 32 to attach the sheath 10 to the member. Because the diameter of the retainer rings may differ from the diameter of the outer tubular member, the attachment links may angle relative to the central axis of the outer member. In the particular embodiment shown in FIGS. 3 and 4, the profile of the elongated outer tubular member 32 is smaller than the profile of the retainer rings 16 so that the attachment links 54 diverge slightly outwardly and distally away from the central axis 52 of the outer tubular member 32.

In operation, it will be appreciated that the self-expanding stent 14 may be radially compressed and telescoped into the annular space between the inside surface of the retainer rings 16 of the delivery sheath 10 and the outside surface of the distal end of the inner tubular member 34. Alternatively, when the stent is made from a shape memory alloy, the stent can be initially mounted over the inner tubular member 34 and subjected to decreased temperature to place the stent into its collapsed position. In order to retain the stent in its compressed delivery state, the sheath is configured such that the hoop strength of the assembly of the retainer rings 16, the connecting links 18 and attachment links 54 is greater than the radial expansion force that will be developed by the stent. It will be appreciated by those skilled in the art that the hoop strength of the sheath is a function of the cross-sectional geometries and the material properties of the respective retainer rings and flexible links. Suitable materials for construction of the components of the sheath include metals, polymers, and fibers. As shown in FIG. 5, the retainer rings 16 may consist of tubular sections having generally constant wall thickness, and the cross-section of the flexible links 18 may be circular. Further, as illustrated by FIG. 1, the longitudinal length of the sheath 10 may be such that all of the stent is captured within the sheath, which, combined with the effect of the symmetrical distribution of the flexible links about the perimeter of the sheath, provides for generally equal distribution of the radial expansion force of the stent throughout the sheath structure.

With continued reference to FIG. 1, the configuration of the sheath 10 in combination with the radiopaque marker 48, located proximally to the stent 14, and the delivery tip 46, located distally, serves to resist axial movement of the stent during delivery. With the sheath thus configured and positioned about the compressed stent to limit both radial and axial movement, the stent delivery system is in its delivery configuration, wherein the outer tubular member 32, including the sheath and the trigger are each at a relatively more distal position relative to the inner tubular member and the hand grasp housing 40 respectively. With the delivery system configured as such, the delivery catheter 20 is inserted into the body lumen and manipulated toward the target site 28.

Other modifications can be made to the delivery sheath 10 wherein the length of the retainer rings 16 is minimized to further increase the flexibility of the sheath and further reduce the frictional contact of the sheath with both the stent 14 and the body lumen 22. The number and wall thickness of the retainer rings 16 and the number, arrangement, and cross-sectional area of the connecting links 18 and attachment links 54 may also be modified to create delivery sheaths of varying increased flexibility. Further, it will be appreciated by those skilled in the art that the retainer rings may be connected by a lattice or mesh material linkage or by many other suitable reduced cross-section or thin-walled tubular links without departing from the spirit and scope of the present invention.

The delivery sheath 10, by covering the peripheral wall of the stent 14, protects the body lumen wall somewhat from abrasion which would otherwise be inflicted by the surface of the stent as the delivery catheter 20 is being advanced within the body lumen. In the absence of such a delivery sheath, the cylindrical elements of the stent would be exposed to the walls of the patient's vasculature and could possibly cause trauma to the walls or cause pieces of plaque to break from the stenosis. Therefore, the use of the flexible, articulate delivery sheath as embodied by the present invention helps to provide stent delivery that is safer and less traumatic to the patient's vasculature.

The flexible connecting links 18 and attachment links 54 of the delivery sheath 10 are configured to perform under both compression and tension loads generated while the stent delivery system is in use. It will be appreciated by those skilled in the art that the flexible links 18 may be under compression as they resist any forces exerted on the sheath in the proximal direction by the lumen wall as the delivery catheter is advanced distally in the body lumen. Thus, in resisting such proximally directed forces, the flexible links serve, in compression, to help maintain spacing of the rings and the position of the sheath relative to the stent 14.

As the catheter 20 is advanced to carry the stent 14 to the desired target, it will be appreciated that the sheath 10 may be advanced through the sharp turns in the tortuous body lumen. During this maneuver, it will be appreciated that the rings 16 serve to hold the stent in its contracted collapsed position shown in FIG. 1. It will be appreciated that, in practice, the rings may be substantially narrower than those shown in FIG. 1 and that their longitudinal spacing will be maintained by the highly flexible links 18. As such sheath is advanced through sharp turns, the links are free to flex with only minimal transverse bending moments placed thereon such that the sheath, over the entire length thereof, can maneuver through a sharp turn with only minimal lateral forces applied thereto by the walls of the body lumen. Consequently, the sheath affords effective column strength for pushing thereof through the lumen and only exhibits minimal resistance to bending about the longitudinal axis so as to minimize any trauma to the walls of the patient's vasculature.

When the delivery catheter reaches the target site to position the stent immediately adjacent the treatment area, as shown in FIG. 1, the delivery sheath 10 may be retracted by drawing back on the pull back handle 38 in the direction of the directional arrows 56 shown in FIG. 2. This movement of the pull back handle 38 within the hand grasp housing 40 of the deployment control assembly 36 translates like movement of the delivery sheath, thereby slidably moving the sheath 10 proximally while the inner tubular member 34 is held in place to gradually expose, and ultimately deploy, the self-expanding stent.

The delivery sheath of the present invention functions to increase the ease and effectiveness of such deployment of the stent. As the sheath is slidably retracted proximally relative to the stent, only minimal frictional resistance forces are created between the sheath and the stent. It will be appreciated by those skilled in the art that one means of reducing such frictional contact between the sheath and the stent is to employ low friction material in the retainer rings, the flexible connecting links and attachment links on any surfaces that directly contact the outside wall of the stent. Metals, including superelastic NiTi, polymers, and fibers for the construction of the rings and links satisfy this low friction criteria. Some specific suitable materials include, but are not limited to, 304V stainless steel, nylon, and woven polyester. In addition, it will be appreciated that the frictional contact between the sheath and the stent is further reduced due to the reduced surface area of the sheath that makes contact with the stent. The area of contact includes the inside surface of the retainer rings and possible line contact existing between the flexible links and the outside wall of the stent. This contact area is significantly less than the area of contact between a self-expanding stent and the inside surface of a typical delivery sheath having a single, continuous tubular wall.

Further, the reduced area of contact between the inner surface of the delivery sheath of the present invention and the outside surface of the self-expanding stent serves to minimize the tendency of the stent to compress the resilient undulations in such stent due to the stent being drawn proximally against the shoulder as the sheath is retracted. This serves to help minimize the buildup of stored energy in such stent while the sheath is being retracted. Consequently, there will be little, if any, rapid longitudinal expansion of the stent as the sheath is drawn proximally again minimizing the tendency of such stent to "jump" distally from the end of the sheath at the end of the deployment process. As a result, a more accurate placement of the stent should be achieved. Accurate stent placement within the target area, as shown in FIG. 2, is important to the function of the stent in maintaining the patency of the body lumen and to minimize stent repositioning, thereby preventing unnecessary additional trauma to the patient's vasculature.

The ability of the connecting links and attachment links to perform as required under both compression and tension is a function of the material of construction and the size and shape of the links. It will be appreciated by those skilled in the art that the frictional contact between the inside surfaces of the sheath and the outside surface of the stent serves to counteract and effectively decrease the compressive forces acting on the sheath and links, when the delivery catheter is advanced distally, while this same frictional contact serves to effectively increase the tensile forces acting on the sheath as it is retracted proximally to deploy the stent. The delivery sheath of the present invention may be optimally configured so as to balance the effects of the frictional contact between the sheath and the stent and the effects of the compression and tension forces on the flexible connecting and mounting links, thereby achieving functional integrity in the sheath while improving stent deployment.

Figure 6:
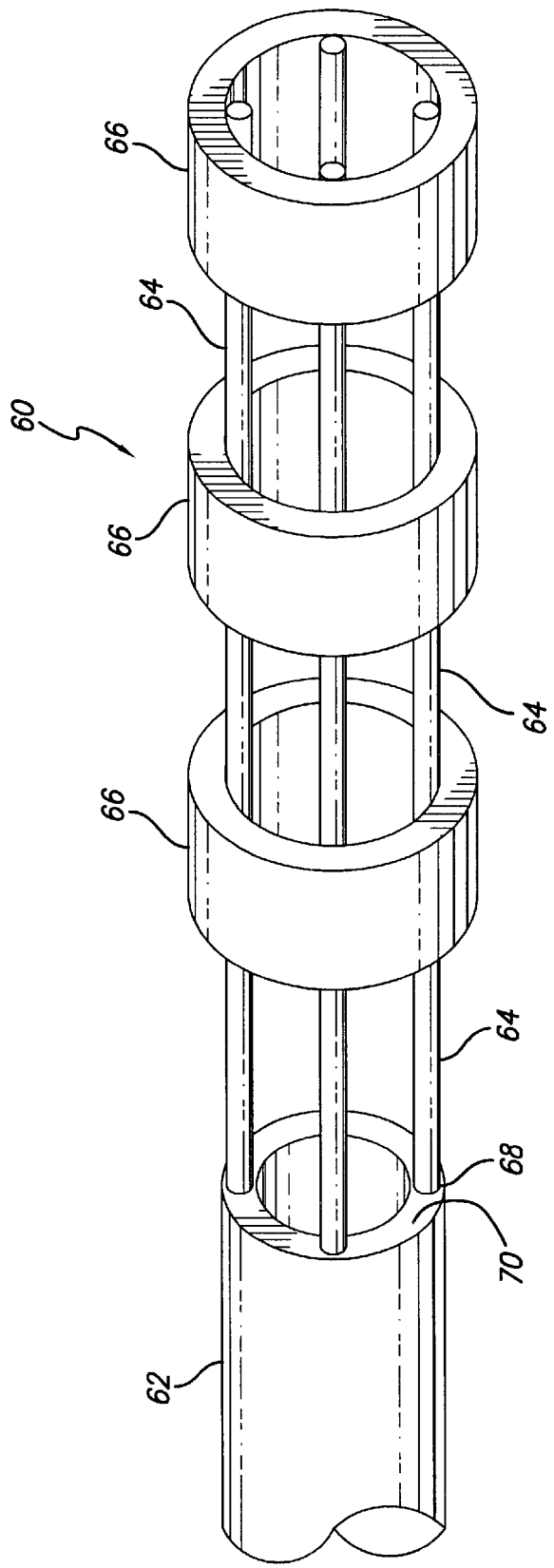
FIG. 6 is a partial perspective view of a second embodiment of the outer tubular member of the stent delivery system of the present invention.

A second embodiment of the delivery sheath 60 of the present invention as shown in FIG. 6 includes, generally, an outer tubular member 62 having an elongated shaft and several elongated, high-flex filaments 64 arranged in a circular pattern, equidistant apart and having mounted thereon high strength, flexible retainer rings 66 in spaced-apart relationship. The proximal ends of the filaments 68 are integrally mounted to the distal end 70 of the shaft.

Figure 7:
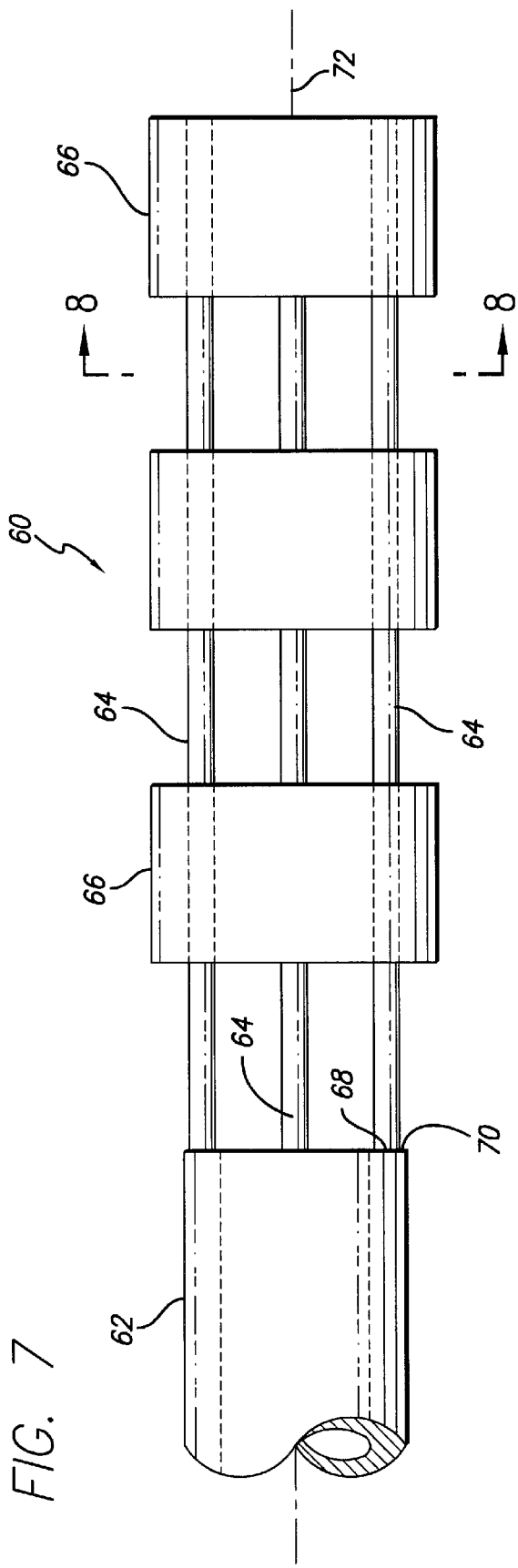
FIG. 7 is a side view of the outer tubular member shown in FIG. 6.
Figure 8:
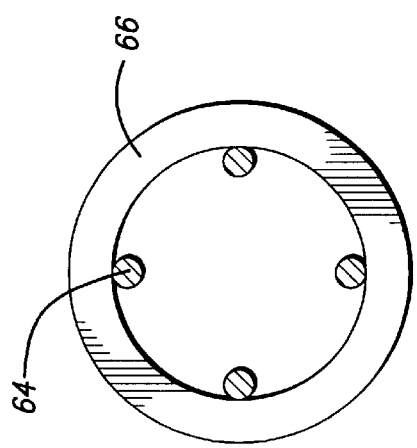
FIG. 8 is a sectional view taken along lines 8—8 of FIG. 7.

The delivery sheath 60, illustrated by FIGS. 7 and 8, may include four elongated highly flexible filaments 64 arranged symmetrically in a circular pattern to mount thereon three tubular retainer rings 66 disposed in spaced apart longitudinal relationship. The filaments are arrayed roughly ninety degrees apart, generally parallel to the central axis 72 of the outer tubular member 62, and are generally circular in cross-section. The three retainer rings are generally evenly spaced along the length of the filaments and may consist of tubular sections having generally constant wall thickness wherein the inside diameter of the rings is roughly equivalent to the outside diameter of the outer member's elongated shaft. The longitudinal length of the sheath 60 may be such that the length of the self-expanding stent is captured within the sheath, which, combined with the effect of the symmetrical distribution of the flexible filaments about the perimeter of the sheath and the generally consistent spacing of the rings, provides for generally equal distribution of the radial expansion force along the length of the stent throughout the length of the delivery sheath 60.

The delivery sheath 60 shown in FIG. 6 exhibits the same advantages of increased flexibility, and thus increased safety in stent delivery, as discussed previously. The added advantage of the delivery sheath illustrated in FIGS. 6–8 is that the filaments 64 essentially act as runners along the area of contact between the inside surfaces thereof and the outside wall of the stent. The effect of this configuration is that the stent may be compressed to a relatively smaller diameter for delivery, since the inside diameter of the sheath is reduced due to the filaments 64 running along the inside of the retainer rings 66, rather than being disposed between them. For most stent delivery systems, this results in a minor increase in profile which usually is not detrimental.

Since the delivery sheath of the present invention has the novel feature of increased longitudinal flexibility, it is particularly well suited for use in delivering stents to target sites requiring tough negotiation of tortuous body lumens. Further, the sheath of the present invention has the added advantage of reduced frictional contact with both the body lumen through which the delivery catheter is being advanced and with the stent during deployment. This advantage of the present invention enables safer and more accurate deployment of a stent in the treatment area of a body lumen. While two particular forms of the present invention have been illustrated and described, it will be apparent that various modifications can be made without departing from the spirit and scope of the invention.

What is claimed is:

1. A flexible stent delivery system, comprising:
   an elongated flexible inner member having a stent mounting region for receiving a stent in a delivery configuration;
   a deployment sheath including a plurality of retainer rings spaced longitudinally apart with flexible links connecting the rings together, the deployment sheath being coaxially disposed over the stent mounting region to form an annular space for mounting the stent in the delivery configuration; and
   means for moving the deployment sheath longitudinally along the inner member.

2. The flexible stent delivery system of claim 1, wherein:
   the retainer rings have an inner surface and and outer surface and include low friction material on the inner surface for providing low frictional contact with the stent.

3. The flexible stent delivery system of claim 1, wherein:
   the retainer rings and links are constructed from metal.

4. The flexible stent delivery system of claim 1, wherein:
   the retainer rings and links are constructed from a polymer material.

5. The flexible stent delivery system of claim 1, wherein:
   the retainer rings and links are constructed from a fiber material.

6. The flexible stent delivery system of claim 1, wherein:
   the deployment sheath includes three retainer rings.

7. The flexible stent delivery system of claim 1, wherein:
   the links are configured with a circular cross-section.

8. The flexible stent delivery system of claim 1, wherein:
   the retainer rings are configured to cooperate with the stent in the compressed delivery configuration to exert a predetermined frictional force resisting relative movement therebetween; and
   the links are configured with sufficient column strength to maintain the retainer rings spaced longitudinally apart as the delivery apparatus is advanced distally within a body lumen.

9. The flexible stent delivery system of claim 1, wherein:
   the hoop strength of the retainer rings and the flexible links is sufficient to maintain the stent in the delivery configuration; and
   the longitudinal lengths of the retainer rings and links in combination are sufficient to cover the length of the stent.

10. The flexible stent delivery system of claim 1, wherein:
    means for moving the deployment sheath is an outer tubular member coaxially disposed and moveable over the inner member that is attached to the deployment sheath.

11. The flexible stent delivery system of claim 10, wherein:
    the links are symmetrically arranged about the longitudinal axis of the outer tubular member and are longitudinally disposed between the retainer rings.

12. The flexible stent delivery system of claim 10, wherein:
    the links include filaments symmetrically arranged about the lonitudinal axis of the outer tubular member and continuous from one end of the deployment sheath to an opposite end.

13. The flexible stent delivery system of claim 1, wherein:
    the stent mounting region is an expandable member and deployment of the stent is achieved by expansion of the expandable member.

14. The flexible stent delivery system of claim 1, wherein:
    the flexible links are disposed to contract the stent and the retainer rings are placed around the flexible links.

15. The flexible stent delivery system of claim 10, wherein:
    the deployment sheath has a diameter greater than the diameter of the outer tubular member.

16. A flexible sheath for use in conjunction with a stent delivery apparatus comprising: a plurality of longitudinally spaced apart retainer rings; and flexible links connecting the retainer rings together; the sheath slidably movable in a longitudinal direction about a stent.

17. The flexible sheath of claim 16, wherein:
    the retainer rings have an inner surface and an outer surface and are configured with low friction material on the inner surface for low frictional contact with the stent.

18. The flexible sheath of claim 16, wherein:
    the retainer rings and links are constructed from metal.

19. The flexible sheath of claim 16, wherein:
    the retainer rings and links are constructed from a polymer material.

20. A flexible sheath of claim 16, wherein:
    the retainer rings and links are constructed from a fiber material.

21. The flexible sheath of claim 16 that includes:
    three retainer rings.

22. The flexible sheath of claim 16, wherein:

the links are configured with a circular cross-section.

23. The flexible sheath of claim 16, wherein:

the links are configured with sufficient column strength to maintain the position of the retainer rings relative to the stent as the stent delivery apparatus is advanced distally within a body lumen; and the links are configured with sufficient tensile strength to enable the retainer rings to move proximally to deploy the stent.

24. The flexible sheath of claim 16, wherein:

the links are symmetrically arranged about the longitudinal axis of the sheath and are longitudinally disposed on an inner surface of the retainer rings.

25. The flexible sheath of claim 16, wherein:

the links include filaments symmetrically arranged about the longitudinal axis of the sheath that are continuous from one end of the sheath to an other end.

* * * * *